(12) United States Patent
Sugimoto

(10) Patent No.: US 7,851,497 B2
(45) Date of Patent: Dec. 14, 2010

(54) BACTERICIDAL COMPOSITION FOR AGRICULTURAL OR HORTICULTURAL USE AND METHOD OF CONTROLLING PLANT DISEASE

(75) Inventor: Koji Sugimoto, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 657 days.

(21) Appl. No.: 11/632,630

(22) PCT Filed: Jul. 14, 2005

(86) PCT No.: PCT/JP2005/013080

§ 371 (c)(1),
(2), (4) Date: Jan. 16, 2007

(87) PCT Pub. No.: WO2006/009085

PCT Pub. Date: Jan. 26, 2006

(65) Prior Publication Data

US 2007/0254936 A1    Nov. 1, 2007

(30) Foreign Application Priority Data

Jul. 16, 2004 (JP) ............................. 2004-210175

(51) Int. Cl.
*A01N 43/50* (2006.01)
*A01P 3/00* (2006.01)

(52) U.S. Cl. .................................................... 514/398
(58) Field of Classification Search ........................ None
See application file for complete search history.

(56) References Cited

U.S. PATENT DOCUMENTS

| 4,731,106 | A | * | 3/1988 | Green et al. | 504/240 |
| 6,096,769 | A | * | 8/2000 | Perlitz et al. | 514/361 |
| 6,375,965 | B1 | * | 4/2002 | Matsuo et al. | 424/405 |

FOREIGN PATENT DOCUMENTS

| EP | 0 298 196 | 1/1989 |
| EP | 0 337 103 A2 | 10/1989 |
| EP | 0 337 103 A3 | 10/1989 |
| GB | 1243519 | 8/1971 |
| JP | 1 131 163 | 5/1989 |
| WO | 98 48628 | 11/1998 |

OTHER PUBLICATIONS http://www.pestmanagement.rutgers.edu/NJinPAS/PesticideRegistration/exemptions18table.htm, pp. 1-9.*
Colby (Weeds. 1967; 15 (1): 20-22, p. 20 provided only).*
C D S Tomlin,"The Pesticide Manual", A World Compendium, pp. 813-816.
G. Lazarovits, et al., "Bioassay of Fungitoxic Compounds on Thin-Layer Chromatograms with Pythium and Phytophthora species", The American Phytopathological Society, vol. 72, No. 1, XP-002572484, 1982, pp. 61-63.

* cited by examiner

*Primary Examiner*—Shanon A Foley
(74) *Attorney, Agent, or Firm*—Oblon, Spivak, McClelland, Maier & Neustadt, L.L.P.

(57) ABSTRACT

To provide an improved fungicidal composition for agricultural or horticultural use, and a method for controlling plant diseases by applying the composition to plants.

A fungicidal composition for agricultural or horticultural use, which comprises at least one imidazole compound of the formula (I):

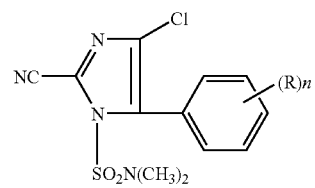

wherein R is a $C_{1-6}$ alkyl group or a $C_{1-6}$ alkoxy group, and n is an integer of from 1 to 5, and propamocarb hydrochloride, as active ingredients; and a method for controlling plant diseases by applying the composition to plants.

12 Claims, No Drawings

BACTERICIDAL COMPOSITION FOR AGRICULTURAL OR HORTICULTURAL USE AND METHOD OF CONTROLLING PLANT DISEASE

TECHNICAL FIELD

The present invention relates to a fungicidal composition for agricultural or horticultural use having plant diseases-controlling effects, particularly effects to prevent and/or cure plant diseases, remarkably improved, and a method for controlling plant diseases by using such a composition.

BACKGROUND ART

EP 298196A discloses that the imidazole compound as an active ingredient of the fungicidal composition for agricultural or horticultural use of the present invention is useful as a pesticide, and it may be used as mixed or combined with another fungicide as the case requires. Further, as a blend pesticidal composition containing the above imidazole compound as an active ingredient, one disclosed in WO98/48628 may be mentioned. Further, propamocarb hydrochloride is a compound disclosed in THE Pesticide Manual Thirteenth Edition, p. 814-816.

Patent Document 1: EP 298196A
Patent Document 2: WO98/48628
Non-patent Document 1: THE Pesticide Manual Thirteenth Edition

DISCLOSURE OF THE INVENTION

Problems to be Solved by the Invention

In their effects for controlling plant diseases, the imidazole compounds of the after-mentioned formula (I) may respectively have problems such that their effects may not be sufficient to a certain plant disease, or their residual effects may be too short, whereby in some application sites, no adequate controlling effects may practically be obtained to plant diseases.

Means to Solve the Problem

The present inventors have conducted a research to solve the above problems as a result have found that by using an imidazole compound of the after-mentioned formula (I) in combination with propamocarb hydrochloride, it is possible to obtain unexpected and further improved effects for controlling plant diseases, as compared with a case where each compound is used alone, and the present invention has been accomplished on the basis of this discovery.

Namely, the present invention provides the following:

(1) A fungicidal composition for agricultural or horticultural use, which comprises at least one imidazole compound of the formula (I):

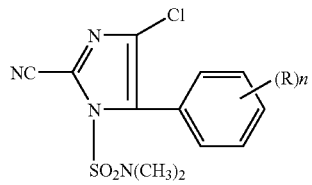

wherein R is a $C_{1-6}$ alkyl group or a $C_{1-6}$ alkoxy group, and n is an integer of from 1 to 5, and propamocarb hydrochloride, as active ingredients.

(2) The fungicidal composition for agricultural or horticultural use according to the above (1), wherein the blend weight ratio of the imidazole compound to the propamocarb hydrochloride is from 1:150,000 to 1,000:1.

(3) A method for controlling plant diseases, which comprises applying a fungicidal composition for agricultural or horticultural use as defined in the above (1) or (2) to plants.

Effects of the Invention

The fungicidal composition for agricultural or horticultural use of the present invention has constant and high controlling effects against crop plants infected with plant diseases, and it is possible to control the plant diseases by using such a composition.

BEST MODE FOR CARRYING OUT THE INVENTION

In the imidazole compound of the formula (I) constituting the fungicidal composition for agricultural or horticultural use of the present invention, the $C_{1-6}$ alkyl group or the alkyl moiety of the $C_{1-6}$ alkoxy group for R, may be $C_{1-6}$ alkyl, such as methyl, ethyl, propyl, butyl, pentyl or hexyl, and such alkyl may be linear or branched. Further, when n is 2 or more, the plurality of R may be the same or different.

The imidazole compounds of the formula (I) include, for example, the following compounds.

4-Chloro-2-cyano-1-dimethylsulfamoyl-5-(4-methylphenyl)imidazole (Compound No. 1)
4-Chloro-2-cyano-1-dimethylsulfamoyl-5-(4-methoxyphenyl)imidazole (Compound No. 2)
4-Chloro-2-cyano-1-dimethylsulfamoyl-5-(4-ethylphenyl)imidazole (Compound No. 3)
4-Chloro-2-cyano-1-dimethylsulfamoyl-5-(3-methyl-4-methoxyphenyl)imidazole (Compound No. 4)

The imidazole compound of the above formula (I) can be prepared by the methods disclosed in e.g. EP 298196A and EP 705823A.

The fungicidal composition for agricultural or horticultural use, which comprises at least one imidazole compound of the above formula (I) and propamocarb hydrochloride, as active ingredients, exhibits excellent fungicidal activities when applied to crop plants e.g. vegetables such as cucumbers, tomatoes or eggplants, cereal crops such as rice or wheat, beans, fruits such as apples, pears, grapes or oranges, or potatoes, which are infected or likely to be infected with pathogenic fungi, and it is suitable for controlling diseases such as powdery mildew, downy mildew, anthracnose, gray mold, green mold, scab, Alternaria leaf spot, bacterial blight, leaf blight, pod and stem blight, ripe rot, late blight, ring leaf-spot, blast, sheath blight, damping-off and southern blight. Further, it exhibits excellent controlling effects against soil-borne diseases caused by phytopathogenic fungi such as *Fusarium, Rhizoctonia, Verticillium, Plasmodiophora* and *Pythium*. The fungicidal composition for agricultural or horticultural use of the present invention has a long residual effect and is excellent in penetration transfer, and thus, it has a preventive effect and/or a curative effect, but it is excellent particularly in the preventive effect.

The fungicidal composition for agricultural or horticultural use of the present invention exhibits excellent controlling effects against diseases by algal fungi, specifically against blast of rice; sheath blight of rice; anthracnose of cucumber; downy mildew of cucumber, melon, cabbage, chinese cabbage, onion, pumpkin or grape; powdery mildew of wheat, barley or cucumber; late blight of potato, red pepper, green pepper, watermelon, pumpkin, tobacco or tomato; speckled leaf blotch of wheat; early blight of tomato; melanose of citrus; common green mold of citrus; scab of pear; Antenaria leaf spot of apple; Shiroiro eki byo of onion; brown rot of watermelon; various diseases such as various gray mold, Sclerotinia rot, rust and bacterial blight; various soil-born diseases caused by phytopathogenic fungi such as *Fusarium, Pythium, Rhizoctonia* and *Verticillium*. Further, it exhibits excellent controlling effects also against diseases by *Plasmodiophora*. The composition further exhibits particularly excellent controlling effects specifically against late blight of potato, red pepper, green pepper, watermelon, pumpkin, tobacco or tomato; or downy mildew of cucumber, melon, cabbage, chinese cabbage, onion, pumpkin or grape.

The plural active ingredients constituting the fungicidal composition for agricultural or horticultural use in the present invention may be blended with various adjuvants to prepare various formulations such as an emulsifiable concentrate, a dust, a wettable powder, an aqueous solution, granules and a suspension, in the same manner as for conventional agricultural formulations. At that time, the compound of the formula (I) and other specific compounds may be mixed and formulated together, or may separately be formulated and then mixed. When such a formulated product is to be practically used, it may be used as it is or after being diluted to a predetermined concentration with a diluting agent such as water. The adjuvants here may, for example, be a carrier, an emulsifier, a suspension agent, a thickener, a stabilizer, a dispersant, a spreading agent, a wetting agent, a penetrating agent, an antifreezer and a defoaming agent, and they may be added as the case requires. The carrier may be divided into a solid carrier and a liquid carrier. The solid carrier may, for example, be an animal or plant powder such as starch, sugar, cellulose powder, cyclodextrin, activated carbon, soybean powder, wheat powder, chaff powder, wood powder, fish powder or dry milk; or a mineral powder such as talc, kaolin, bentonite, organic bentonite, calcium carbonate, calcium sulfate, sodium hydrogencarbonate, zeolite, diatomaceous earth, white carbon, clay, alumina, silica, sulfur powder or slaked lime. The liquid carrier may, for example, be water; a vegetable oil such as soybean oil or cotton oil; an animal oil such as beef tallow or whale oil; an alcohol such as ethyl alcohol or ethylene glycol; a ketone such as acetone, methyl ethyl ketone, methyl isobutyl ketone or isophorone; an ether such as dioxane or tetrahydrofuran; an aliphatic hydrocarbon such as kerosene, lamp oil, liquid paraffin or cyclohexane; an aromatic hydrocarbon such as toluene, xylene, trimethylbenzene, tetramethylbenzene or solvent naphtha; a halogenated hydrocarbon such as chloroform or chlorobenzene; an acid amide such as dimethylformamide; an ester such as ethyl acetate or a glycerin ester of a fatty acid; a nitrile such as acetonitrile; a sulfur-containing compound such as dimethylsulfoxide, or N-methyl-2-pyrrolidone or N,N-dimethylformamide. The spreading agent may, for example, be sodium alkylsulfate, sodium alkylbenzenesulfonate, sodium lignin sulfonate, polyoxyethylene alkyl ether, polyoxyethylene lauryl ether, polyoxyethylene alkyl aryl ether or polyoxyethylene sorbitan fatty acid ester.

In the fungicidal composition for agricultural or horticultural use of the present invention, a suitable blend weight ratio of at least one compound of the formula (I) to the propamocarb hydrochloride, is usually from 1:150,000 to 1,000:1, preferably from 1:10,000 to 1,000:1, more preferably from 1:200 to 200:1. The most preferred blend weight ratio is from 1:100 to 1:1.

The present invention also includes a method for controlling plant diseases, which comprises applying the fungicidal composition for agricultural or horticultural use of the present invention to plants. The concentrations of the active ingredients in the fungicidal composition for agricultural or horticultural use of the present invention vary depending upon the crop plant to be treated, the method to be used, the formulation, the dose, the season for application, the type of pathogenic fungi and can not generally be defined. However, in the case of foliar treatment, the concentrations of the active ingredients are such that usually, the compound of the above formula (I) is from 0.01 to 1,000 ppm, preferably from 0.3 to 500 ppm, and the propamocarb hydrochloride is from 0.1 to 10,000 ppm, preferably from 0.5 to 5,000 ppm.

Now, some preferred embodiments of the fungicidal composition for agricultural or horticultural use of the present invention will be exemplified. However, the present invention is by no means thereby restricted.

(1) A fungicidal composition for agricultural or horticultural use, which comprises at least one compound of the formula (I) and propamocarb hydrochloride, as active ingredients.

(2) The fungicidal composition for agricultural or horticultural use according to (1) wherein the weight ratio of said at least one compound of the formula (I) to the propamocarb hydrochloride is from 1:10,000 to 1,000:1.

(3) The fungicidal composition for agricultural or horticultural use according to (1), wherein the weight ratio of said at least one compound of the formula (I) to the propamocarb hydrochloride is from 1:200 to 200:1.

(4) The fungicidal composition for agricultural for horticultural use according to (1), wherein the weight ratio of said at least one compound of the formula (I) to the propamocarb hydrochloride is from 1:100 to 1:1.

EXAMPLES

Now, Test Examples relating to the present invention will be described, but the present invention is by no means thereby restricted.

Test Example 1

Test on Preventive Effect Against Cucumber Downy Mildew

Cucumber (cultivar: Suyo) was cultivated in a polyethylene pot having a diameter of 7.5 cm, and when the cucumber reached two-leaf stage, a drug solution having the respective test compounds adjusted to the predetermined concentrations, was applied in a sufficient amount (20 ml) by means of a spray gun. After the applied solution dried, the cucumber was sprayed and inoculated with a suspension of spores of cucumber downy mildew and kept in a humidified chamber at 20° C. for 4 hours. Thereafter, the cucumber was kept in a thermostatic chamber at 20° C. for 7 days, whereupon the lesion area ratio in the first leaf was investigated, and the control value was obtained by the following formula. The results are shown in Table 1. Here, the test was carried out in double series.

The lesion area ratio in non-treated area was obtained in the same manner as in the treated area except that instead of the drug solution, water was applied by means of a spray gun.

Control value=$(b-a)/b \times 100$ where a is the lesion area ratio in treated area, and b is the lesion area ratio in non-treated area.

Further, a theoretical value can be calculated by the Colby formula. If the experimental value is higher than the theoretical value by the Colby formula, the fungicidal composition for agricultural or horticultural use of the present invention has a synergistic effect for controlling the plant disease. In this context, the theoretical values by the Colby formula are also shown in brackets ( ) in Table 1.

TABLE 1

| propamocarb hydrochloride | Compound No. 1 Control value in the test on preventive effect against cucumber downy mildew (theoretical value) | | |
|---|---|---|---|
| | 0.13 ppm | 0.03 ppm | 0 ppm |
| 4000 ppm | 100 (93) | 70 (30) | 30 |
| 2000 ppm | 100 (91) | 60 (10) | 10 |
| 1000 ppm | 100 (90) | 70 (0) | 0 |
| 0 ppm | 90 | 0 | |

The lesion area ratio in the non-treated area was 100.

Test Example 2

Test on Curative Effect Against Cucumber Downy Mildew

Cucumber (cultivar: Suyo) was cultivated in a polyethylene pot having a diameter of 7.5 cm, and when it reached two-leaf stage, the cucumber was sprayed and inoculated with a suspension of spores of cucumber downy mildew and kept in a humidified chamber at 20° C. for 4 hours. Then, after drying the crop plant, a drug solution having the respective test compounds adjusted to the predetermined concentrations, was applied in a sufficient amount (20 ml) by means of a spray gun. After the sprayed solution dried, it was kept in a thermostatic chamber at 20° C. for 7 days, whereupon the lesion area ratio in the first leaf was investigated, and the control value was obtained by the following formula. The results are shown in Table 2. Here, the test was carried out in double series.

The lesion area in non-treated area was obtained in the same manner as in the treated area except that instead of the drug solution, water was applied by means of a spray gun.

Control value=$(b-a)/b \times 100$ where a is the lesion area ratio in treated area, and b is the lesion area ratio in non-treated area.

Further, a theoretical value can be calculated by the Colby formula. If the experimental value is higher than the theoretical value by the Colby formula, the fungicidal composition for agricultural or horticultural use of the present invention has a synergistic effect for controlling the plant disease. In this context, the theoretical values by the Colby formula are also shown in brackets ( ) in Table 2.

TABLE 2

| propamocarb hydrochloride | Compound No. 1 Control value in the test on curative effect against cucumber downy mildew (theoretical value) | | |
|---|---|---|---|
| | 500 ppm | 125 ppm | 0 ppm |
| 4000 ppm | 100 (93) | 100 (30) | 30 |
| 2000 ppm | 100 (92) | 100 (20) | 20 |
| 1000 ppm | 100 (91) | 100 (10) | 10 |
| 0 ppm | 90 | 0 | |

The lesion area ratio in the non-treated area was 100.

Test Example 3

Test on Preventive Effect Against Tomato Late Blight

Tomato (cultivar: Ponderosa) was cultivated in a polyethylene pot having a diameter of 7.5 cm, and when it reached four-leaf stage, a drug solution having the respective test compounds adjusted to the predetermined concentrations, was applied in a sufficient amount (20 ml) by means of a spray gun. After the applied solution dried, the tomato was sprayed and inoculated with a zoosporangia suspension of tomato late blight and kept in a humidified chamber at 20° C. for 6 hours. Then, it was kept in a thermostatic chamber at 20° C. for 3 days. Then, the disease outbreak index of each leaf was investigated by the following standards, and the degree of disease outbreak was obtained by the following formula.

Disease outbreak index 0: No lesion is observed.
Disease outbreak index 1: The lesion area is less than 10% of the leaf area.
Disease outbreak index 2: The lesion area is from 10% to less than 25% of the leaf area.
Disease outbreak index 3: The lesion area is from 25% to less than 50% of the leaf area.
Disease outbreak index 4: The lesion area is at least 50% of the leaf area.

Further, using the degree of disease outbreak, the control value is obtained by the following formula, and the results are shown in Table 3. Here, the test was carried out in double series.

The degree of disease outbreak in non-treated area was obtained in the same manner as in the treated area except that instead of the drug solution, water was applied by means of a spray gun.

Degree of disease outbreak=$[(0 \times A + 1 \times B + 2 \times C + 3 \times D + 4 \times E)/\{4 \times (A+B+C+D+E)\}] \times 100$ where A is the number of leaves with disease outbreak index 0, B is the number of leaves with disease outbreak index 1, C is the number of leaves with disease outbreak index 2, D is the number of leaves with disease outbreak index 3, and E is the number of leaves with disease outbreak index 4.

Control value=$(b'-a')/b' \times 100$ where a' is the degree of disease outbreak in treated area, and b' is the degree of disease outbreak in non-treated area.

Further, a theoretical value can be calculated by the Colby formula. If the experimental value is higher than the theoretical value by the Colby formula, the fungicidal composition for agricultural or horticultural use of the present invention has a synergistic effect for controlling the plant disease. In such a context, the theoretical values by the Colby formula are also shown in brackets ( ) in Table 3.

TABLE 3

| propamocarb hydrochloride | Compound No. 1 Control value in the test on preventive effect against tomato late blight (theoretical value) | |
|---|---|---|
| | 0.5 ppm | 0 ppm |
| 4000 ppm | 92 (67) | 0 |
| 2000 ppm | 100 (67) | 0 |
| 1000 ppm | 100 (67) | 0 |
| 0 ppm | 67 | |

The degree of disease outbreak in the non-treated area was 100.

The entire disclosure of Japanese Patent Application No. 2004-210175 filed on Jul. 16, 2004 including specification, claims, drawings and summary is incorporated herein by reference in its entirety.

The invention claimed is:

1. A fungicidal composition for agricultural or horticultural use, which comprises 4-chloro-2-cyano-1-dimethylsulfamoyl-5-(4-methylphenyl)imidazole and propamocarb hydrochloride, as active ingredients.

2. The fungicidal composition for agricultural or horticultural use according to claim 1, wherein the blend weight ratio of 4-chloro-2-cyano-1-dimethylsulfamoyl-5-(4-methylphenyl)imidazole to the propamocarb hydrochloride is from 1:150,000 to 1,000:1.

3. A method for controlling plant diseases, which comprises applying a fungicidal composition for agricultural or horticultural use as defined in claim 1 or 2 to plants.

4. The fungicidal composition as defined in claim 1, wherein the 4-chloro-2-cyano-1-dimethylsulfamoyl-5-(4-methylphenyl)imidazole to the propamocarb hydrochloride is present in a ratio of from 1:10,000 to 1,000:1.

5. The fungicidal composition as defined in claim 1, wherein the 4-chloro-2-cyano-1-dimethylsulfamoyl-5-(4-methylphenyl)imidazole to the propamocarb hydrochloride is present in a ratio of from 1:200 to 200:1.

6. The fungicidal composition as defined in claim 1, wherein the 4-chloro-2-cyano-1-dimethylsulfamoyl-5-(4-methylphenyl)imidazole to the propamocarb hydrochloride is present in a ratio of 1:100 to 1.

7. The method as defined in claim 3, wherein the 4-chloro-2-cyano-1-dimethylsulfamoyl-5-(4-methylphenyl)imidazole is applied in a ratio of from 1:10,000 to 1,000:1.

8. The method as defined in claim 3, wherein the 4-chloro-2-cyano-1-dimethylsulfamoyl-5-(4-methylphenyl)imidazole is applied in a ratio of from 1:200 to 200:1.

9. The method as defined in claim 3, wherein the 4-chloro-2-cyano-1-dimethylsulfamoyl-5-(4-methylphenyl)imidazole to the propamocarb hydrochloride is applied in a ratio of 1:100 to 1:1.

10. The method as defined in claim 3, wherein the plant is a crop plant, a cereal crop or a fruit plant.

11. The method as defined in claim 3, wherein the plant disease is one or more of powdery mildew, downy mildew, anthracnose, gray mold, green mold, scab, Alternaria leaf spot, bacterial blight, leaf blight, pod and stem blight, ripe rot, late blight, ring leaf-spot, blast, sheath blight, damping-off and southern blight.

12. The method as defined in claim 3, wherein the plant disease is a soil-borne disease caused by a phytopathogenic fungi selected from the group consisting of *Fusarium, Rhizoctonia, Verticillium, Plasmodiophora* and *Pythium*.

* * * * *